US005861269A

United States Patent [19]
Visor et al.

[11] Patent Number: 5,861,269
[45] Date of Patent: *Jan. 19, 1999

[54] METHODS FOR REMOVING INTERFERENCES DUE TO ENDOGENOUS DEHYDROGENASES IN ENZYME ASSAYS

[75] Inventors: Jill McCornack Visor, Pacifica; Shireen Hussain Khan, La Jolla; Anthony Joseph DeLizza, Los Altos, all of Calif.

[73] Assignee: Dade Behring Marburg GmbH, Marburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 742,767

[22] Filed: Nov. 1, 1996

[51] Int. Cl.$^6$ ..................................................... C12Q 1/32
[52] U.S. Cl. ........................... 435/26; 435/184; 435/962; 435/975
[58] Field of Search ................................. 435/25, 26, 28, 435/184, 188, 962, 975

[56] References Cited

U.S. PATENT DOCUMENTS

| | | | |
|---|---|---|---|
| 4,242,446 | 12/1980 | Madappally et al. | 435/15 |
| 4,810,633 | 3/1989 | Bauer et al. | 435/25 |
| 4,937,047 | 6/1990 | Kobayashi et al. | 422/56 |
| 5,141,854 | 8/1992 | Kaufman et al. | 435/26 |
| 5,294,540 | 3/1994 | Daniel et al. | 435/25 |
| 5,372,934 | 12/1994 | Bussian et al. | 435/26 |
| 5,429,932 | 7/1995 | Detwiler et al. | 435/26 |
| 5,610,025 | 3/1997 | White et al. | 435/25 |

FOREIGN PATENT DOCUMENTS

| | | |
|---|---|---|
| 0 037 742 A2 | 10/1981 | European Pat. Off. . |
| 0 140589 A1 | 5/1985 | European Pat. Off. . |
| 0 239 990 | 10/1987 | European Pat. Off. . |
| 0 239 990 A2 | 10/1987 | European Pat. Off. . |
| 3303098 A1 | 8/1984 | Germany . |
| WO 92/16649 | 10/1992 | WIPO . |
| 97/16562 | 5/1997 | WIPO . |
| WO97/16562 | 5/1997 | WIPO . |

OTHER PUBLICATIONS

Thompson, et al., *Clinical Chemistry*, vol. 40(8), 1594–5 (1994); "False–Positive Ethanol in Clinical and Postmortem Sera by Enzymatic Assay: Elimination of Interference by Measuring Alcohol in Protein–Free Ultrafiltrate".
Nine, et al., *Journal of Analytical Toxicology*, vol. 19, 192–196 (1995); "Serum–Ethanol Determination: Comparison of Lactate and Lactate Dehydrogenase Interference in Three Enzymatic Assays".
Soo Ja Kim, et al., *Journal of Biological Chemistry*, vol. 244(2), 231–235 (1969); "Nonpolar Interactions of Inhibitors with the Nicotinamide Adenine Dinucleotide–binding Sites of L–α–Glycerophosphate Dehydrogenase".
Vincenzini, et al., *Physiological Chemistry and Physics and Medical NMR*, vol. 17, 279–295 (1985); "Detergents as Selective Inhibitors and Inactivators of Enzymes".
Bacchi, et al., *Journal of Bacteriology*, vol. 98(1), 23–28 (1969); "Effects of Some Antitumor Agents on Growth and Glycolytic Enzymes of the Flagellate Crithidia".
Lindena, et al., *J. Clin. Chem. Clin. Biochem.*, vol. 24(1), 35–47 (1986); "Catalytic Enzyme Activity Concentration in Tissues of Man, Dog, Rabbit, Guinea Pig, Rat and Mouse".
Lambeir, et al., *Eur. J. Biochemistry*, vol. 198(2), 429–435 (1991); "The Cytosolic and Glycosomal glyceraldehyde–3–phosphate dehydrogenase from *Trypanosoma brucei*: Kinetic properties and comparison with homologous enzymes".
Thedes–Reynolds, et al., *Clinical Chemistry*, vol. 39, 1143 (abstract 0111) (1993); "False Positive Ethanol Results by Emit®".
Osama, et al., *Biochimica et Biophsicia Acta*, vol. 752, 251–258 (1983); "Inhibition of Brain Prostaglandin D Synthetase and Prostaglandin D2Dehydrogenase By Some Saturated and Unsaturated Fatty Acids".
Yoon, et al., *Journal of General Microbiology*, vol. 135, 245–250 (1989); "Site–directed Inhibition of *Haemphilus influenzae* Malate Dehydrogenase".
Lambier, et al., *Eur. J. Biochemistry*, vol. 198(2), 429–435 (1991); "The Cytosolic and Glycosomal Glyceraldehyde–3–phosphate Dehydrogenase from *Trypanosoma brucei*: Kinetic properties and comparison with homolgous enzymes".
Pongsawasdi, et al., *Archives of Biochemistry and Biophysics*, vol. 238(1), 280–289 (1985); "Studies of the Coenzyme Binding Site of Rat Ovarian 20α–Hydroxysteriod Dehydrogenase".
Zollner, *Handbook of Enzyme Inhibitors/Part B*, Ed. 2, DE Weinholm, VCH., 1993, 545 biz.; EN.
Thompson, W., False Positive Ethanol in clinical and Postmortem Sera by Enzymatic Assay, Clinical Chemistry, 40(8), 1994.
Vincenzini M., Detergents as Selective Inhibitors and Inactivators of Enzymes, Physiological Chemistry and Physics and Medical NMR, vol. 17 279–295 1985.

*Primary Examiner*—Ralph Gitomer
*Attorney, Agent, or Firm*—Theodore J Leitereg

[57] ABSTRACT

The present invention is an improvement in a method using a reporter dehydrogenase for detecting the presence of an analyte in a sample in which endogenous dehydrogenases present in the sample interfere with the detection of the analyte. The improvement is the inclusion of an inhibitor of the endogenous dehydrogenase in the assay medium. The improvement finds particular utility in the measurement of ethyl alcohol using alcohol dehydrogenase as the reporter enzyme when lactate and lactate dehydrogenase present in the sample interfere with the detection of the analyte. Particulary effective inhibitors which prevent this interference are fatty acids, such as, agaric acid and lauric acid, and alkyl sulfate salts, such as, sodium dodecyl sulfate and sodium decyl sulfate.

12 Claims, No Drawings

METHODS FOR REMOVING INTERFERENCES DUE TO ENDOGENOUS DEHYDROGENASES IN ENZYME ASSAYS

BACKGROUND OF THE INVENTION

1. Field of the Invention

This invention relates to diagnostic assays for the detection of both haptens and macromolecules based on the measurement of the activity of a dehydrogenase enzyme. These assays are widely used in both clinical and non-clinical settings for the detection of analytes of interest. A significant problem in these assays is interference caused by endogenous dehydrogenases leading to elevated signals and false-positive responses. Furthermore, due to the presence of endogenous dehydrogenases in whole blood, assays based on measurement of dehydrogenase activity cannot be used with whole blood samples.

One solution that has been proposed to circumvent this problem has been to perform the assay on protein-free ultrafiltrates. However, this is cumbersome and incorporates an extra filtration step requiring special equipment into the assay procedure. It also necessitates that the test be done by trained personnel. It would be desirable to have an assay which does not require the use of specialized equipment and trained personnel. Such an assay would allow testing in a wider array of environments, more rapidly and at lower cost.

2. Summary of Related Art

False-Positive Ethanol in Clinical and Postmortem Sera by Enzymatic Assay: Elimination of Interference by Measuring Alcohol in Protein-Free Ultrafiltrate; William C. Thompson, Deepak Malhotra, David P. Schammel, Walter Blackwell, Michael E. Ward and Amitava Dasgupta; *Clinical Chemistry,* 40(8), 1594–5 (1994); disclosed that removing lactate dehydrogenase by ultrafiltration eliminates interference in the Emit® Ethyl Alcohol assay.

Serum-Ethanol Determination: Comparison of Lactate and Lactate Dehydrogenase Interference in Three Enzymatic Assays; Jeffrey S. Nine, M. Moraca, M. A. Virji and K. N. Rao; *Journal of Analytical Toxicology,* 19, 192–196 (1995); showed that elevated serum-lactate and LDH concentrations can result in varying degrees of false-positive ethyl alcohol concentrations in enzymatic assays.

Nonpolar Interactions of Inhibitors with the Nicotinamide Adenine Dinucleotide-binding Sites of L-α-Glycerophosphate Dehydrogenase; Soo Ja Kim and Bruce M. Anderson; *Journal of Biological Chemistry,* 244(2), 231–5 (1969); discloses the inhibition of L-α-glycerophosphate dehydrogenase by a homologous series of aliphatic carboxylic acids.

Detergents as Selective Inhibitors and Inactivators of Enzymes; M. T. Vincenzini, F. Favilli, M. Stio, P. Vanni and C. Treves; *Physiological Chemistry and Physics and Medical NMR,* 17, 279–295 (1985); investigated effect of detergents on pyridine-dependent dehydrogenases.

Effects of Some Antitumor Agents on Growth and Glycolytic Enzymes of the Flagellate Crithidia; Cyrus J. Bacchi, Edward I. Ciaccio and Lois E. Koren; *Journal of Bacteriology,* 98(1), 23–28 (1969); disclosed that agaric acid was highly inhibitory to malate and α-glycerophosphate dehydrogenase.

Catalytic Enzyme Activity Concentration in Tissues of Man, Dog, Rabbit, Guinea Pig, Rat and Mouse; J. Lindena, Ute Sommerfeld, Cornelia Hopfel and I. Trautschold; *J. Clin. Chem. Clin. Biochem.,* 24(1), 35–47 (1986); disclosed the presence of dehydrogenase activity in postmortem tissue.

The Cytosolic and Glycosomal glyceraldehyde-3-phosphate dehydrogenase from *Trypanosoma brucei:* Kinetic properties and comparison with homologous enzymes; A. M. Lambeir, A. M. Loiseau, D. A. Kuntz, F. M. Vellieux, P. A. Michels and F. R. Opperdoes; *Eur. J. Biochem* 198(2), 429–35 (1991); studied the effects of agaric acid on the trypanosome NAD-dependent glyceraldehyde-3-phosphate dehydrogenase enzymes.

False Positive Ethanol Results by Emit®; Kathy Thedes-Reynolds and George F. Johnson; *Clin. Chem.,* 39, 1143 (Abstract 0111) (1993); reported that the false positive ethanol result was probably due to lactate dehydrogenase catalyzed conversion of serum lactate and reagent NAD to NADH and pyruvate.

SUMMARY OF THE INVENTION

This invention relates to methods of removing interferences due to endogenous dehydrogenases in assays using a dehydrogenase as a reporter enzyme. It has unexpectedly been discovered that incorporation of an inhibitor of dehydrogenase enzymes into the assay matrix eliminates the aforementioned elevated signals and false-positive results. Accordingly, one aspect of the present invention is an improvement in a method for detecting the presence of an analyte in a sample suspected of containing such analyte. The method comprises forming an assay medium comprising the sample and assay reagents. The assay reagents comprise a first dehydrogenase enzyme whose activity is related to the presence of the analyte. The presence of a second dehydrogenase enzyme in the sample interferes with the measurement of this activity. The improvement comprises including in the assay medium an effective amount of an inhibitor of the second dehydrogenase enzyme thus preventing interference by the second dehydrogenase enzyme. Thereby, the activity of the first dehydrogenase enzyme can be accurately related to the presence of the analyte. The inhibitor of the second dehydrogenase enzyme may be included as, or part of, the assay reagents or added to the sample. Other aspects of the invention include such methods as above in which the first dehydrogenase is an alcohol dehydrogenase and the second dehydrogenase is a lactate dehydrogenase. Also forming part of the invention is the improvement in which the inhibitor of the second dehydrogenase is an amphiphilic species comprising a hydrophobic moiety and a hydrophilic moiety which may be anionic or cationic. The invention also includes kits for conducting assays for detecting the presence of an analyte in a sample containing an endogenous dehydrogenase. The kit comprises in packaged combination a reporter dehydrogenase and an inhibitor of the endogenous dehydrogenase.

DETAILED DESCRIPTION OF THE INVENTION

Definitions and General Parameters

The following definitions are set forth to illustrate and define the meaning and scope of the various terms used to describe the invention herein.

The term "alkyl" refers to a branched or straight chain acyclic, monovalent saturated hydrocarbon radical of one to thirty carbon atoms. Examples include heptyl($-C_7H_{15}$), 2-ethylheptyl($-C_9H_{20}$), dodecyl($-C_{12}H_{25}$) and cetyl($-C_{16}H_{33}$).

The term "lower-alkyl", refers to an alkyl radical of one to six carbon atoms. This term is further exemplified by such radicals as methyl, ethyl, n-propyl, isopropyl, isobutyl, sec-butyl, n-butyl and tert-butyl, n-hexyl and 3-methylpentyl.

The term "alkenyl" refers to a branched or straight chain acyclic, monovalent unsaturated hydrocarbon radical of one to thirty carbon atoms containing at least one carbon—carbon double bond. Examples include 1-decenyl, 2-decenyl and 9,12-octadecadienyl.

The term "alkynyl" refers to a branched or straight chain acyclic, monovalent unsaturated hydrocarbon radical of one to thirty carbon atoms containing at least one carbon—carbon triple bond. Examples include 1-decynyl, 2-decynyl and 3-dodecynyl.

The term "amphiphilic species" refers to a molecule having a water soluble (hydrophilic) portion and a water insoluble organic (hydrophobic) portion such as, for example, lauryl alcohol, lauric acid, sodium stearate, capric acid, sodium decyl sulfate or alkylammonium salts such as, for example, n-decylammonium chloride.

The term "fatty acid" refers to an organic monobasic acid derived from a hydrocarbon by the equivalent of oxidation of a methyl group to a carboxylic group, COOH. Fatty acids include saturated acids, $C_{2N+1}COOH$, such as acetic acid, hexanoic acid and lauric acid; unsaturated acids $C_{2N-1}COOH$, such as dimethylacrylic acid, oleic acid and linoleic acid; acetylenic acids $C_{2N-3}COOH$; and polyunsaturated acids $C_{2N-5}COOH$ such as linolenic acid.

The term "halo" refers to fluoro, bromo, chloro and iodo.

The term "dehydrogenase" refers to an enzyme of the oxidoreductase class (EC1) that catalyzes the transfer of hydrogen or electrons from a donor compound to an acceptor compound. Dehydrogenases are usually designated according to the substrate (donor compound) that is oxidized, e.g., alcohol dehydrogenase refers an enzyme which oxidizes alcohols by transferring hydrogen from the alcohol to an acceptor and lactate dehydrogenase refers to and enzyme which oxidizes lactic acid to pyruvic acid by transferring hydrogen to an acceptor. Representative dehydrogenases include alcohol dehydrogenase, lactate dehydrogenase, isocitrate dehydrogenase and malate dehydrogenase.

The term "effective amount" refers to the amount which is necessary to create the desired effect. In the case where the desired effect is to determine accurately the presence of the analyte by inhibiting the activity of an interfering endogenous dehydrogenase, an "effective amount" of an inhibitor is that amount of inhibitor which allows such an accurate determination. Typically, an "effective amount" of the inhibitor will inhibit the activity of the endogeneous dehydrogenase by about 90%, preferably about 98%, and more preferably about 99%.

The term "signal producing system" refers to the species necessary to generate a signal that relates to the presence or amount of analyte in a sample. It is utilized in assays for analytes and may have one or more components, at least one component being a reporter dehydrogenase. It may also include cofactors used by the reporter dehydrogenase. The signal producing system includes all of the reagents required to produce a measurable signal.

The present invention includes improvements in methods for the detection of analytes whose detection is based on the activity of a dehydrogenase enzyme employed as a reporter molecule or label(reporter dehydrogenase). Typically, the activity of the dehydrogenase is related to the amount of analyte present. Frequently, such detection systems are subject to interference from endogenous dehydrogenases present in the sample comprising the analyte. The improvement comprises including in the assay medium an inhibitor of the endogeneous dehydrogenases. Selective inhibition of the endogenous dehydrogenases permits accurate measurement of activity corresponding to the reporter dehydrogenase enzyme which in turn can be related to the amount of analyte present.

The analyte may be present in samples such as bodily fluids or tissues, e.g., whole blood, serum, urine, saliva, plasma, amniotic fluid, cerebrospinal fluid, post mortem cardiac tissue, kidney, liver, gastric fluid, muscle, fat, spleen, brain, pleural fluid, vitreous humor etc. The analyte may be any of a wide variety of materials, such as drugs, naturally occurring physiological compounds (e.g. proteins, antibodies and hormones), pollutants and the like. The precise nature of some of the analytes together with numerous examples thereof are disclosed int U.S. Pat. No. 4,299,916 to Litman et al., particularly at columns 16 to 23, the disclosure of which is incorporated by reference. Typically, the analyte is a substrate for the reporter dehydrogenase enzyme and the activity of the reporter dehydrogenase is measured by detecting the product of the enzymatic reaction. The product can be either the species to which the analyte is converted or the product from an obligate cofactor of the enzymatic reaction. Endogenous dehydrogenases, which can employ the analyte as a substrate, interfere with the enzymatic reaction. Similarly, endogenous dehydrogenases that use as an obligate cofactor the same cofactor as is used by the reporter dehydrogenase may also interfere with the enzymatic reaction. Under such circumstances, the endogenous dehydrogenase catalyzes the conversion of cofactor to a detectable species independent of the presence of the analyte thus giving a false positive result.

The improvement of the present invention can be used with any assay for an analyte employing a reporter dehydrogenase as a label. Both competitive and non-competitive protocols may be employed. In a competitive protocol, analyte and reporter dehydrogenase-labeled analyte compete for binding to a receptor for the analyte and the extent of labeled analyte binding to receptor is determined. The extent of binding is related to the analyte present and is determined by measuring the amount of signal produced by the label reporter dehydrogenase. An example of such an assay can be found in Rubenstein et al., U.S. Pat. No. 3,817,837.

As mentioned above, the present invention has application to the determination of a wide variety of analytes wherein one of a wide variety of reporter dehydrogenases may be used. The Emit® ethanol assay is an example, by way of illustration and not limitation, of such an assay using a reporter dehydrogenase. In the Emit® ethanol assay, alcohol dehydrogenase (ADH) catalyzes the oxidization of ethyl alcohol to acetaldehyde using the coenzyme NAD (β-nicotinamide adenine dinucleotide), which is concurrently reduced to form NADH according to the following equation:

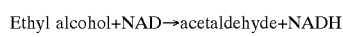

Ethyl alcohol+NAD→acetaldehyde+NADH

ADH activity as measured by the production of NADH is thus related to the amount of ethyl alcohol in the sample. If an NAD dependent dehydrogenase is present in the sample, it will, in the presence of its substrate, produce NADH irrespective of whether or not alcohol is present in the sample. For example, if lactate and lactate dehydrogenase are present in a sample, lactate will be converted to pyruvate with the concomitant production of NADH as a detectable species even in the absence of ethyl alcohol, thus giving a false positive result. Other dehydrogenases may use NADP (β-nicotinamide adenine dinucleotide phosphate) instead of NAD. The present invention discloses a method of preventing this by including in the assay medium an inhibitor of the endogenous dehydrogenase.

Specifically, the Emit® ethanol assay is subject to interference with samples containing lactate and lactate dehydrogenase. Lactate dehydrogenase catalyzes the conversion of lactate to pyruvate with the concomitant production of NADH, thus producing a signal even in the absence of ethyl alcohol. We have found that including an inhibitor of lactate dehydrogenase in the assay medium prevents this false positive result. It has been found that carboxylic acids, both singly and in combination, and salts of alkyl sulfates are particularly effective. Any dehydrogenase based assay subject to interference from an endogenous dehydrogenase is amenable to such an improvement. Any dehydrogenase based assay system which is subject to interference due to the activity of a second endogeneous dehydrogenase can be improved in such a manner by including an inhibitor of the second dehydrogenase in the assay medium.

The improvement has been exemplified above using an assay for alcohol which employs alcohol dehydrogenase as the reporter dehydrogenase and NAD as the obligate cofactor. Other dehydrogenases can also be employed as the reporter dehydrogenase. Other enzymes which employ NAD or NADP as cofactor include glucose-6-phosphate dehydrogenase, malate dehydrogenase, lactate dehydrogenase, mannitol-1-phosphate dehydrogenase, glycerol dehydrogenase, glyoxylate reductase, glutamate dehydrogenase, isocitrate dehydrogenase and the like. Similarly, the interfering endogenous dehydrogenase can also include the enzymes listed above. Alternative cofactors used by dehydrogenase enzymes include cytochromes, $O_2$, $H_2O_2$ and the like.

The choice of inhibitor will be a function of the nature of the reporter dehydrogenase, the endogenous dehydrogenase and the assay protocol. Determination of the inhibitory activity of a particular compound towards a dehydrogenase enzyme can be determined by methods well known to one of skill in the art. Typically, the activity of the dehydrogenase enzyme is determined in the presence of varying amounts of the inhibitory compound, see (Nonpolar Interactions of Inhibitors with the Nicotinamide Adenine Dinucleotide-binding Sites of L-α-Glycerophosphate Dehydrogenase, by Soo Ja Kim and Bruce M. Anderson; *Journal of Biological Chemistry*, 244(2), 231–5 (1969)). Preferably, the inhibitor will selectively inhibit the endogenous dehydrogenase. Such selective inhibition may be achieved by kinetic control or equilibrium control. Thus, an inhibitor which inhibits both the endogenous dehydrogenase and the reporter dehydrogenase may be used if the rate of inhibition of the endogenous dehydrogenase is sufficiently faster than the inhibition of the reporter dehydrogenase. Alternatively, the assay protocol may be such that the inhibitor is added to the sample prior to adding the reporter dehydrogenase and/or obligate cofactor (if a cofactor is being used). Inhibition may be reversible or irreversible. If inhibition is nonselective, reversible inhibitors will normally require that the assay time be short relative to the time frame of reversal of inhibition.

The inhibitors used in this invention are those having a hydrophobic moiety linked to a polar hydrophilic moiety. The hydrophilic moiety may be anionic or cationic. The structure of such an inhibitor is represented by the formula L-D wherein L is a hydrophobic moiety and D is a polar anionic or cationic moiety. L will be a saturated or unsaturated hydrocarbon chain represented by the formulas $C_NH_{2N+1}$, $C_NH_{2N-1}$, $C_NH_{2N-3}$, $C_NH_{2N-5}$, etc. depending on the number of degrees of unsaturation present in the hydrocarbon chain. N will range from 1 to 30, more typically from about 5 to 25 and preferably from 8 to 16. L may also be optionally substituted with nonionic groups such as halo, SH and OH. D will consist of a short carbon chain or carbocycle of 1–6 carbon atoms substituted with at least one polar group X, normally 1–5 polar groups X, preferably 1–3 polar groups X, and more preferably 1 polar group X, selected from the group consisting of —OH, —$CO_2H$, —$SO_3H$, —$PO_3H$, —$OSO_3H$, —PO(OR)OH, —PO(OH)$_2$, —OPO(OH)$_2$, —OPO(OR)OH and —$NH_2$, wherein R represents a lower alkyl group, and where D is represented by the formulas $C_nX_aH_{2n+1-a}$ or $C_nX_aH_{2n-1-a}$ corresponding to D having a carbon chain or carbocycle respectively where n=1–6 and a=1–5. Such mixed hydrophobic/hydrophilic species have been postulated to simultaneously bind to the hydrophobic binding site and the pyrophosphate binding site of NAD/NADP dependent dehydrogenases ("Nonpolar Interactions of Inhibitors with the Nicotinamide Adenine Dinucleotide-binding Sites of L-α-Glycerophosphate Dehydrogenase; Soo Ja Kim and Bruce M. Anderson," *Journal of Biological Chemistry*, 244(2), 231–5 (1969).

Particularly preferred are inhibitors in which L is a hydrocarbon chain of 8–16 carbon atoms, and D is a 1 to 3 carbon chain carrying at least one carboxylate group($CO_2^-$) or sulfate group ($OSO_3^-$). Such carboxylic acids and sulfates are useful in assays in which NAD or NADP dependent dehydrogenases are used as the reporter dehydrogenase. Particularly preferred in such assays are lauric acid, agaric acid, linoleic acid, myristoleic acid, and sodium decyl sulfate, especially when the interfering endogenous dehydrogenase is lactate dehydrogenase.

The inhibitor may be a combination of acids. Certain acids are more effective in combination with a lower molecular weight acid such as, for example, oxalic acid, S-fluoropyruvic acid, malonic acid, 2-ketomalonic acid, dihydroxy malonic acid, oxalomalic acid, malic acid, 2-ketoglutaric acid, 2-oxobutyric acid, succinic acid, glycolic acid, isophthalic acid, glyoxylic acid, etc. Often, using a lower molecular weight acid in combination with a fatty acid inhibitor allows the use of the fatty acid at a lower concentration than otherwise. This is advantageous when the solubility of the fatty acid is a limiting factor. For example, capric acid used in combination with oxalic acid in the molar ratio 1:2 (capric acid:oxalic acid) is more effective at eliminating false positives in the EMIT® ethanol assay than when used independently. Typically the molar ratio of lower molecular weight acid to fatty acid used is about 1:3, preferably 1:1, more preferably 2:1, even more preferably 4:1.

Another class of preferred inhibitors are the alkali and alkali metal salts of alkyl sulfates. Sodium and potassium salts are particularly preferred. The alkyl group is represented by the moiety $C_nH_{2n+1}$ where n ranges from 1 to 30, preferably from 6 to 20, and more preferably from 8 to 12.

While various orders of addition may be employed, preferably the inhibitor is added to the sample followed by the addition of the reporter dehydrogenase (and cofactor if needed). Desirably, the first combination will be followed by an incubation to allow for equilibration of the sample with the inhibitor. Various dilutions and incubations may be employed in the assay. That is, before or concomitantly with each addition, additional aqueous medium may be added to provide for accurate transfer of reagents, increase the volume as required by the measuring instrument, or the like. Incubation steps will normally vary from about 10 seconds to 6 hours, usually from about 10 seconds to 1 hour, preferably from about 30 seconds to 30 minutes, more preferably from about 1 minutes to 30 minutes.

The assay medium may be a wholly liquid phase which may be wholly or partially aqueous. It may also include reagents immobilized on a solid phase, such as for example, when the reporter dehydrogenase is immobilized on beads or a paper strip and exposed to the sample. The assay medium will normally be buffered in the range of about pH 5 to 10, more usually in the range of about 6 to 9.5 and preferably in the range of about 7 to 9.5. Various buffers may be employed, though one buffer may be preferred in a particular situation. Illustrative buffers include borate, phosphate, barbital, Tris etc.

The temperature during the various states of addition and incubation will generally be in the range of about 10° to 50° C., more usually in the range of about 15° to 45° C., preferably in the range 25° to 37° C.

The invention also includes kits for determining the presence of an analyte in a sample containing an interfering endogenous dehydrogenase. The kits comprise in packaged combination assay reagents comprising a reporter dehydrogenase and an inhibitor of the endogenous dehydrogenase. Additionally, the kit may contain an obligate cofactor, such as, for example, NAD or NADP. The assay reagents may be packaged in the same or separate containers. Surface active additives, including bulking agents such as BLG (β-lactoglobulin), PEG (polyethylene glycols), RSA, BSA, Mod-u-cyte, Sol-u-pro or the like; defoamers and surfactants such as Tween-20, Plurafac A38, Triton X-100, Pluronic 25R2, or the like; and other materials commonly used in the art can be added to improve solubility and reduce nonspecific binding of reagents and analyte to surfaces. Antimicrobial agents such as azide, thimerosal, gentamicin and the like can be added to assay reagents in order to extend the storage life of the reagents. The kits can further include other packaged reagents for conducting an assay including members of the signal producing system, ancillary reagents, and so forth.

The following examples further describe the specific embodiments of the invention. These are typical illustrative examples and are intended to describe and not to limit the scope of the invention.

EXAMPLES

Materials

Carboxylic acids such as capric acid, oxalic acid, lauric acid and myristoleic acid are available from commercial vendors such as Aldrich Chemical Co., Milwaukee, Wis. Agaric acid is available from Janssen Chimica, New Brunswick, N.J. Sodium dodecyl sulfate is available from Sigma Chemical Co., St. Louis, Mo. Sodium decyl sulfate is available from Oakwood Products, West Columbia, S.C.

Emit® assay reagents for the Emit® Ethyl Alcohol Assay were obtained from Syva Company, San Jose, Calif.

Methods

The ability of inhibitors to prevent false positive results with samples containing endogenous dehydrogenases was determined by employing the Emit® Ethyl Alcohol Assay available from Syva Company, San Jose, Calif. (Part No. 9K219). The assays were performed on the Cobas Mira-S analyzer (Roche Diagnostics Inc., Nutley, N.J.) according to the manufacturer's instructions using the protocol provided by Syva Company. Briefly, the Emit® Ethyl Alcohol Assay consists of two reagents, Reagent 1 and Reagent 2. Reagent 1 contains Tris buffer, stabilizers and preservatives. Reagent 2 contains alcohol dehydrogenase, nicotinamide adenine dinucleotide ($NAD^+$), bulking agents, stabilizers, surfactants and preservatives. Reagent 2 is shipped in dry form and is reconstituted according to the manufacturer's instructions. To perform the assay, Reagent 1 and Reagent 2 %ere added to the sample. Following mixing and incubation, the change in absorbance at 340 nm was monitored. The reaction is linear, and calibration was achieved by single point calibration using a 100 mg/dL (0.10%) calibrator, supplied by Syva Company. The calculation of results was not required. The instrument prints the quantitative result.

In the following examples, results reported under the column Current Emit® refer to results observed using the Emit® Ethyl Alcohol assay in the absence of inhibitor. Results reported under the column Inhibitor Emit® refer to results observed using the Emit® Ethyl Alcohol assay in the presence of the specified inhibitor. Results reported under the column GC refer to confirmatory results obtained using gas chromatography. Examples 1–6 were performed using serum samples. Example 7 used whole blood samples

Example I

Improved Assay with Agaric Acid

Agaric acid was dissolved in Emit® Ethyl Alcohol Reagent 1 by stirring with heat to a concentration of 25 mM. The agaric acid turned the colorless reagent 1 into a faint yellow solution. The solution was cooled to room temperature. The pH of the solution was measured and adjusted to the pH of the Emit® Ethyl Alcohol Reagent 1 (pH 9.0) with a small volume of 10N NaOH. The patient samples used to test the efficacy of agaric acid were serum samples confirmed negative for ethanol by gas chromatography, but were falsely elevated by the Emit® Ethyl Alcohol Assay. These discrepant samples were analyzed using the Emit® Ethyl Alcohol Assay side by side with the assay containing agaric acid. The data below show that the elevated ethanol results observed in the Emit® Ethyl Alcohol Assay were eliminated in the presence of agaric acid.

| | Total Ethanol (mg/dl) | | |
|---|---|---|---|
| | | Reference Method | |
| Sample ID | Current Emit ® | GC | Agaric Acid Emit ® |
| A91-234 | 69.1 | <5 | 3.2 |
| A93-218 | 127.3 | <5 | 2.2 |
| A93-259 | 105.9 | <5 | 1.5 |
| A93-48 | 78.7 | <5 | 0.3 |
| A93-229 | 86.1 | <5 | 6.1 |
| A93-239 | 103.5 | <5 | 6.5 |
| A93-269 | 116.1 | <5 | 3.9 |
| A93-105 | 75.5 | <5 | 10.9 |
| A93-112 | 40.5 | <5 | 2.9 |
| A91-120 | 46.0 | <5 | -0.3 |
| A93-265 | 66.7 | <5 | 3.0 |

Example 2

Improved Assay with Lauric Acid

Following the procedure of Example 1 the following results were obtained when lauric acid was substituted for agaric acid. Lauric acid was prepared in Reagent 1 at a concentration of 50 mM. No heat was required. The data below show that the elevated ethanol results observed in the Emit® Ethyl Alcohol Assay were eliminated in the presence of lauric acid.

Total Ethanol (mg/dl)

| | Reference Method | | |
|---|---|---|---|
| Sample ID | Current Emit ® | GC | Lauric Acid Emit ® |
| A93-10 | 61.5 | <10 | 3.3 |
| A92-98 | 94.8 | 0 | 1.8 |
| A93-48 | 82.1 | ND | 6.5 |
| A93-105 | 50.0 | <5 | 6.7 |
| A93-212 | 45.1 | 13 | 15.7 |

Example 3

Improved Assay with Myristoleic Acid

Following the procedure of Example 1, the following results were obtained when myristoleic acid was substituted for agaric acid at a concentration of 50 mM in Reagent 1. The data below show that the elevated ethanol results observed in the Emit® Ethyl Alcohol Assay were eliminated in the presence of myristoleic acid.

Total Ethanol (mg/dl)

| | Reference Method | | |
|---|---|---|---|
| Sample ID | Current Emit ® | GC | Myristoleic Acid Emit ® |
| A93-10 | 61.5 | <10 | 0.4 |
| A92-98 | 94.8 | 0 | 0.9 |
| A93-48 | 82.1 | ND | 1.4 |
| A93-105 | 50.0 | <5 | -0.7 |
| A93-212 | 45.1 | 13 | 14.9 |

Example 4

Improved Assay with Capric Acid+Oxalic Acid

Capric acid was dissolved in the Emit® Ethyl Alcohol Assay Reagent 1 at 50 mM, twice the final Reagent 1 concentration. Oxalic acid was also prepared in the Emit® Ethyl Alcohol Assay Reagent 1 at 100 mM, twice the final Reagent 1 concentration. Both compounds readily dissolved into Reagent 1 to form colorless solutions. The addition of capric acid to Reagent 1 does not cause a shift in the final pH; however the addition of oxalic acid to Reagent 1 requires a pH adjustment to pH 9.0 using a small volume of 5N HCl. The two solutions were then mixed 1:1 by volume to prepare the Emit® Ethyl Alcohol Assay Reagent 1 cocktail containing capric acid and oxalic acid. The data show that the discrepant ethanol quantitations were significantly reduced in the presence of capric acid/oxalic acid.

Total Ethanol (mg/dl)

| | Reference Method | | |
|---|---|---|---|
| Sample ID | Current Emit ® | GC | Capric + Oxalic Acid Emit ® |
| A93-105 | 48.5 | <5 | 10.3 |
| A93-120 | 29.1 | <5 | 1.2 |
| A93-229 | 83.5 | ND | 10.5 |
| A93-259 | 76.6 | ND | 1.7 |
| A93-265 | 47.1 | ND | 4.8 |
| A93-269 | 77.6 | ND | 3.6 |

ND = not detected

Example 5

Improved Assay with Sodium Dodecyl Sulfate (SDS)

Following the procedure of Example 1 the following results were obtained when sodium dodecyl sulfate was substituted for agaric acid at a concentration of 12.5 mM in Reagent 1. The data below shows that the elevated ethanol results observed in the Emit® Ethyl Alcohol Assay were eliminated in the presence of sodium dodecyl sulfate.

Total Ethanol (mg/dl)

| | Reference Method | | |
|---|---|---|---|
| Sample ID | Current Emit ® | GC | SDS Emit ® |
| A92-01 | 76.5 | ND | 1.2 |
| A92-299 | 48.7 | ND | 2.9 |
| A93-8 | 107.4 | ND | 1.0 |
| A93-12 | 12.4 | ND | 0.8 |
| A93-14 | 68.2 | NDET | 8.3 |
| A93-21 | 15.2 | NDET | 4.0 |
| A93-26 | 12.8 | NDET | 1.2 |
| A93.27 | 44.5 | ND | 0.9 |
| A93.44 | 48.8 | NDET | 5.8 |
| A93.45 | 84.3 | ND | 1.7 |
| A93-48 | 81.5 | NDET | 5.4 |
| A93-55 | 75.0 | NDET | 2.1 |
| A93-57 | 81.0 | NDET | 2.3 |
| A93-88 | 19.1 | NDET | 1.6 |
| A93-93 | 116.0 | NDET | 0.9 |
| A93-94 | 113.7 | ND | 4.3 |
| A93-97 | 86.3 | <5 | 1.9 |
| A93-99 | 83.2 | ND | 2.4 |
| A93-101 | 10.5 | ND | 0.6 |
| A93-102 | 42.1 | ND | 7.2 |
| A93-105 | 82.1 | <5 | 7.9 |
| A93-109 | 115.3 | NDET | 7.7 |
| A93-111 | 104.1 | NDET | 0.3 |
| A93-112 | 46.1 | ND | 0.5 |
| A93-118 | 81.8 | NDET | 0.8 |
| A93-119 | 77.5 | ND | 1.7 |
| A93-120 | 19.6 | <5 | 1.8 |
| A93-121 | 26.8 | NDET | 8.7 |
| A93-123 | 48.8 | ND | -3.1 |
| A93-212 | 42.2 | 13.0 | 15.1 |
| A93-218 | 108.2 | NDET | 6.5 |
| A93-221 | 82.2 | ND | 1.9 |
| A93-225 | 93.9 | ND | 1.7 |
| A93-227 | 33.2 | NDET | 1.5 |
| A93-228 | 32.0 | NDET | 1.0 |
| A93-229 | 63.7 | NDET | 6.9 |
| A93-239 | 89.0 | NDET | 1.3 |
| A93-240 | 54.0 | ND | 0.3 |
| A93-251 | 38.6 | NDET | 1.4 |
| A93-255R | 31.2 | ND | 1.9 |
| A93-256 | 81.3 | ND | 2.3 |
| A93-259 | 70.4 | NDET | 4.4 |
| A93-260 | 46.7 | NDET | 1.2 |
| A93-265 | 48.2 | NDET | 0.8 |
| A93-269 | 100.4 | NDET | 6.1 |
| A91-252 | 12.2 | ND | 7.6 |
| A91-285 | 18.8 | ND | 4.9 |
| L-2361S | 95.2 | ND | -1.0 |
| L-2362S | 254.3 | ND | 189.2 |
| L-2363S | 63.7 | ND | -0.4 |
| L-2366s | 66.9 | ND | 7.8 |
| L-2379 | 96.5 | ND | 1.9 |
| L-2381 | 31.9 | ND | 1.3 |
| A93-2P | 28.0 | 0 | 0.8 |
| A93-4P | 63.6 | ND | 1.7 |
| A93-8P | 23.6 | 0 | 0.6 |
| A93-10P | 45.0 | <10 | 15.4 |
| A93-20P | 20.8 | 0 | 0.6 |
| A93-26P | 71.0 | 0 | 4.5 |
| A93-28P | 17.8 | ND | -3.2 |
| A93-42P | 73.6 | ND | 14.0 |
| A93-53P | 98.2 | ND | 11.4 |
| A93-94P | 24.7 | 0 | 1.6 |
| A93-98P | 84.9 | 0 | 7.5 |
| A93-187 | 57.0 | NDET | 1.1 |
| A93-246 | 60.9 | NDET | 1.4 |
| A94-91 | 18.6 | NDET | 1.5 |
| A94-115 | 17.8 | NDET | -0.2 |
| A94-116 | 89.3 | NDET | 1.4 |

-continued

Total Ethanol (mg/dl)

Reference Method

| Sample ID | Current Emit ® | GC | SDS Emit ® |
|---|---|---|---|
| A94-118 | 80.5 | NDET | 3.7 |
| A93-122 | 88.9 | NDET | 8.1 |
| A94-126 | 71.9 | NDET | 1.1 |
| A94-130 | 98.1 | NDET | 6.4 |
| A94-133 | 87.0 | NDET | 12.7 |
| A94-134 | 81.4 | NDET | 4.0 |
| A94-136 | 64.4 | NDET | 38.0 |
| A94-144 | 61.4 | NDET | 0.6 |
| A94-173 | 27.8 | NDET | 1.1 |
| A93-200 | 69.4 | ND | 2 |
| A93-271 | 10.1 | NDET | 0.0 |
| A93-272R | 53.3 | ND | 0.4 |
| A93-272Y | 28.9 | ND | 1.6 |
| A93-291 | 83.7 | ND | −1.3 |
| A93-100 | 26.4 | <5 | 8.4 |
| A91-112 | 29.4 | NDET | 1.6 |
| A91-181 | 40.4 | ND | 1.1 |
| A91-185 | 51.9 | NDET | 1.9 |
| A93-192 | 54.9 | 8 | 13.4 |
| A93-2001 | 24.2 | ND | 0.3 |
| A91-234 | 52.9 | NDET | −11.2 |

NDET = None Detected
ND = Not Determined

Example 6

Improved Assay with Sodium Decyl Sulfate

Following the procedure of Example 1 the following results were obtained when sodium decyl sulfate was substituted for agaric acid. Decyl sulfate was used at a final concentration of 60 mM. The data below show that the elevated ethanol results observed in the Emit® Ethyl Alcohol Assay were eliminated in the presence of sodium decyl sulfate.

Total Ethanol (mg/dl)

Reference Method

| Sample ID | Current Emit ® | Sodium Decyl Sulfate Emit ® | GC |
|---|---|---|---|
| A90-104 | 14.4 | 0.0 | NDET |
| A93-226 | 26.6 | 1.8 | NDET |
| A93-230 | 8.6 | 0.1 | NDET |
| A93-238 | 20.5 | 0.0 | NDET |
| A93-250 | 50.6 | −0.3 | NDET |
| A93-270 | 7.1 | 0.4 | NDET |
| A93-281 | 75.4 | −0.8 | NDET |
| A93-287 | 60.5 | −2.0 | NDET |
| AV93-63 | 4.2 | −1.1 | NDET |
| AV93-64 | 85.9 | −0.3 | NDET |
| AV93-65 | 55.6 | −2.6 | <5 |
| AV93-66 | 7.1 | 1.2 | NDET |
| AV93-67 | 0.9 | −1.1 | <5 |
| AV93-69 | 93.4 | −2.4 | NDET |
| AV93-71 | 28.5 | −8.9 | NDET |
| AV93-72 | 92.6 | 3.8 | <5 |
| AV93-74 | 73.7 | 41.2 | 53 |
| AV93-75 | 39.5 | −5.4 | NDET |
| AV93-77 | 75.5 | −0.6 | <5 |
| AV93-78 | 71.4 | −0.2 | NDET |
| AV93-79 | 13.8 | −0.3 | NDET |
| AV93-80 | 88.9 | −0.9 | <5 |
| A94-43 | 9.1 | −0.4 | NDET |
| A94-44 | 35.8 | −1.7 | NDET |
| A94-46 | 95.9 | −8.0 | NDET |
| A94-49 | 4.4 | −0.2 | NDET |
| A94-55 | 80.4 | −2.5 | NDET |
| A94-56 | 62.3 | −5.1 | NDET |
| A94-57 | 8.4 | 0.5 | NDET |
| A94-59 | 102.5 | −0.7 | NDET |
| A94-62 | 95.1 | −2.0 | NDET |
| A94-63 | 21.1 | −0.6 | NDET |
| A94-64 | 26.8 | −0.2 | NDET |
| A94-65 | 13.5 | 0.0 | NDET |
| A94-67 | 69.3 | −2.3 | NDET |
| A94-69 | −4.7 | 2.2 | NDET |
| A94.70 | 56.8 | −1.4 | NDET |
| A94-73 | 95.7 | 0.2 | NDET |
| A94-74C | 72.7 | 4.4 | 5 |
| A94-76 | 99.9 | 0.6 | NDET |
| A94-77 | 20.5 | −0.5 | NDET |
| A94-78 | 73.8 | −0.9 | NDET |
| A94-79 | 54.8 | −0.2 | NDET |
| A94-84 | 46.4 | −2.1 | NDET |
| A94-86 | 105.8 | −0.3 | NDET |
| A94-87 | 26.6 | 0.9 | NDET |
| A94-88 | 76.8 | 0.3 | NDET |
| A94-89 | 67.8 | −0.4 | NDET |
| A94-91 | 78.0 | 1.0 | NDET |
| A94-93 | 51.1 | −1.0 | NDET |
| A94-97 | 48.4 | 1.7 | NDET |
| A94-98 | 54.5 | 0.3 | NDET |
| A94-102 | 13.9 | −0.4 | NDET |
| A94-104 | 78.4 | −0.7 | NDET |
| AV94-3 | 79.5 | −0.9 | NDET |
| A94-4 | 98.1 | −0.9 | NDET |
| AV94-06A | 26.4 | 0.0 | NDET |
| AV94-06S | 46.0 | 11.2 | 14 |

NDET = None Detected

Example 7

Improved Assays with Whole Blood Samples

Using the procedures described in Examples 1 and 4 but using a whole blood sample instead the following results were obtained.

Total Ethanol (mg/dl)

Reference Method

| Sample ID | Current Emit ® | GC | Agaric Acid Emit ® | Capric + Oxalic Acid Emit ® |
|---|---|---|---|---|
| 1 | 168.3 | 70 | 74.6 | 63.6 |
| 2 | 198.0 | 106 | 104.4 | 104.5 |
| 3 | 226.3 | 79 | 88.2 | 101.2 |
| 4 | 96.1 | 43 | 50.0 | 47.0 |
| 5 | 395.1 | 324 | 332.1 | 325.0 |

The data shows the improved accuracy of the Emit® Ethyl Alcohol Assay in the presence of agaric acid or capric acid/oxalic acid for the analyses of whole blood ethanol samples versus the current Emit® product.

What is claimed is:

1. In a method for detecting the presence of an ethanol analyte in a sample suspected of containing said ethanol analyte, said method comprising forming an assay medium comprising said sample and assay reagents, said assay reagents comprising an alcohol dehydrogenase enzyme whose activity is related to the presence of said analyte and relating the activity of said alcohol dehydrogenase enzyme to the presence of said ethanol analyte wherein the presence of a lactate dehydrogenase enzyme in said sample interferes with the measurement of such activity, the improvement comprising including in said assay medium an inhibitor of said lactate dehydrogenase enzyme in an amount effective to inhibit the activity of said lactate dehydrogenase enzyme wherein said inhibitor is selected from the group consisting of lauric acid, agaric acid, capric acid, linoleic acid and myristoleic acid.

2. The method of claim 1 wherein said inhibitor is added to said sample.

3. The method of claim 1 wherein said inhibitor is included in said assay reagents.

4. The method of claim 1 wherein said alcohol dehydrogenase is an NAD or NADP dependent dehydrogenase.

5. The method of claim 1 wherein said assay reagent comprising an inhibitor of said lactate dehydrogenase is combined with said sample before combining said assay reagent comprising an alcohol dehydrogenase enzyme.

6. The method of claim 1 wherein said inhibitor is employed in combination with a lower molecular weight carboxylic acid.

7. The method of claim 6 wherein said lower molecular weight carboxylic acid is oxalic acid.

8. A kit for conducting an assay for detecting the presence of an ethanol analyte in a sample containing an endogenous lactate dehydrogenase, said kit comprising in packaged combination a reporter alcohol dehydrogenase and an inhibitor of the endogenous lactate dehydrogenase wherein said inhibitor is present in an amount effective to inhibit the activity of said endogenous dehydrogenase and wherein said inhibitor is selected from the group consisting of lauric acid, agaric acid, capric acid, linoleic acid and myristoleic acid.

9. The kit of claim 8 wherein said packaged combination comprises at least two containers.

10. The kit of claim 8 wherein said inhibitor is employed in combination with a lower molecular weight carboxylic acid.

11. The kit of claim 10 wherein said lower molecular weight carboxylic acid is oxalic acid.

12. A method for detecting the presence of an ethanol analyte in a sample suspected of containing said analyte, wherein said sample contains a lactate dehydrogenase which interferes with the detection of said ethanol analyte, said method comprising forming an assay medium comprising said sample, assay reagents and an inhibitor of said lactate dehydrogenase, said assay reagents comprising the coenzyme NAD and an alcohol dehydrogenase enzyme whose activity is related to the presence of said ethanol analyte, said inhibitor being present in an amount effective to inhibit the activity of said lactate dehydrogenase enzyme wherein said inhibitor is selected from the group consisting of agaric acid, lauric acid, and a combination of capric acid plus oxalic acid, and relating the activity of said alcohol dehydrogenase enzyme to the presence of said ethanol analyte.

* * * * *

UNITED STATES PATENT AND TRADEMARK OFFICE
CERTIFICATE OF CORRECTION

PATENT NO. : 5,861,269
DATED : January 19, 1999
INVENTOR(S) : Jill McCornack Visor, et. al.

It is certified that error appears in the above-identified patent and that said Letters Patent is hereby corrected as shown below:

Column 8, Line 4: Delete "%ere" and insert --were--.

Signed and Sealed this

Twentieth Day of July, 1999

Attest:

Q. TODD DICKINSON

*Attesting Officer*     *Acting Commissioner of Patents and Trademarks*